(12) United States Patent
Lopez et al.

(10) Patent No.: US 7,619,111 B2
(45) Date of Patent: Nov. 17, 2009

(54) STEREOSELECTIVE METHOD FOR PREPARING A CHIRAL FLUORINATED MOLECULE

(75) Inventors: Joseph Lopez, Aumes (FR); Gérard Rajoharison, Vernaison (FR); Jean-Serge Ferlut, Lyons (FR)

(73) Assignee: Rhodia Chimie, Aubervilliers (FR)

( * ) Notice: Subject to any disclaimer, the term of this patent is extended or adjusted under 35 U.S.C. 154(b) by 0 days.

(21) Appl. No.: 11/664,515

(22) PCT Filed: Oct. 4, 2005

(86) PCT No.: PCT/FR2005/002434

§ 371 (c)(1),
(2), (4) Date: Aug. 17, 2007

(87) PCT Pub. No.: WO2006/037887

PCT Pub. Date: Apr. 13, 2006

(65) Prior Publication Data

US 2008/0071108 A1    Mar. 20, 2008

(30) Foreign Application Priority Data

Oct. 4, 2004    (FR) .................................. 04 10450

(51) Int. Cl.
*C07C 69/63*    (2006.01)

(52) U.S. Cl. ..................................................... 560/227
(58) Field of Classification Search .................. None
See application file for complete search history.

(56) References Cited

U.S. PATENT DOCUMENTS 3,100,225 A    8/1963    Zappel et al.
3,283,018 A    11/1966    Christe et al.

FOREIGN PATENT DOCUMENTS

DE    41 31 242 A1    4/1993
GB    899127    *    6/1962

OTHER PUBLICATIONS

Lewis et al., "The Kinetics and Stereochemistry of the Decomposition of Secondary Alkyl Chlorosulfites", J. Am. Chem.Soc., vol. 74, Jan. 20, 1952, pp. 308-311.

* cited by examiner

*Primary Examiner*—Paul A Zucker
(74) *Attorney, Agent, or Firm*—Buchanan, Ingersoll & Rooney, P.C.

(57) ABSTRACT

A stereoselective method for preparing a chiral fluorinated molecule by converting a compound having a —OSOF group, a fluorosulfite, attached to a chiral carbon atom into a fluorinated compound by replacing the —OSOF group attached the chiral carbon with a fluorine atom where the compound having the fluorine atom in place of the —OSOF group has an inverse configuration relative to the —OSOF group.

40 Claims, No Drawings

STEREOSELECTIVE METHOD FOR PREPARING A CHIRAL FLUORINATED MOLECULE

This application is the United States national stage of International Patent Application No. PCT/FR2005/002434, filed Oct. 4, 2005, which is incorporated by reference herein in its entirety and relied upon, and which claims priority of Application No. 04/10450, filed Oct. 4, 2004, in France.

The present invention relates to a method for preparing chiral fluorinated molecules, especially fluorinated molecules having a fluorine atom carried by an asymmetric carbon atom having the (R) or (S) configuration, located a (alpha) to an ester or ketone group. It relates in particular to the preparation of methyl (R)-2-fluoropropionate (R2F).

Such compounds are products that are valuable industrially especially as intermediates for the synthesis of plant protection agents or of insecticides.

U.S. Pat. No. 3,100,225 describes a method for producing organic compounds containing fluorine by thermal decomposition of the corresponding fluorosulfite compound in the presence of a tertiary amine. That document does not teach a stereoselective method.

U.S. Pat. DE 4131242 describes a stereoselective route for the synthesis of R2F, which involves the following two steps:

sulfomethylation step

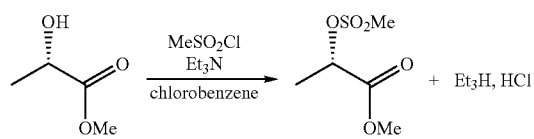

step of exchange by means of KF:

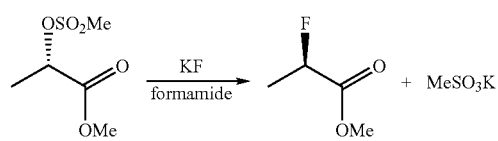

That route for obtaining R2F functions well from the chemical point of view but has a major disadvantage: the generation of large amounts of effluent with a very high reprocessing cost.

The authors of the present invention have therefore set themselves the object of developing a novel stereoselective method for obtaining such fluorinated molecules, which method gives a satisfactory yield starting from inexpensive reagents and does not generate large amounts of effluent.

The authors have succeeded in developing a method which achieves that object and which yields optically active products having a given configuration, especially having an optical purity equal to or greater than 95%.

The invention accordingly relates to a stereoselective method for preparing a chiral fluorinated molecule, in which:
(i) a molecule containing a C*—OSOF unit (referred to as fluorosulfite compound hereinafter) is introduced into a reactor;
(2i) thermal decomposition of that molecule is carried out in the presence of a nucleophilic catalyst;
(3i) the resulting fluorinated molecule, containing a C*—F unit having the inverse configuration relative to the starting C*—OSOF unit, is recovered.

"Nucleophilic" is understood as meaning a catalyst having an atom that is capable of yielding a duplet. There are suitable compounds containing a tertiary nitrogen atom, fluoride anion sources and mixtures or complexes thereof.

The catalyst can be a tertiary amine, e.g. the catalyst can be selected from: triethylamine, diisopropylethylamine, tri-n-propylamine, tri-n-butylamine, methyl-dibutylamine, methyldicyclohexylamine, ethyldiisopropylamine, N,N-diethylcyclo-hexylamine, pyridine, 4-dimethylaminopyridine, N-methylpiperidine, N-ethyl-piperidine, N-n-butylpiperidine, 1,2-dimethylpiperidine, N-methylpyrrolidine, 1,2-dimethylpyrrolidine, dimethylaniline, picoline, and mixtures thereof.

It is also possible to use amides or formamides containing a tertiary nitrogen atom, such as, for example, dimethylformamide, dimethylacetamide.

It is also possible to use urea derivatives, such as ureas substituted by alkyl groups, for example tetramethylurea.

As fluoride anion source there may be mentioned basic fluorides such as KF, quaternary ammonium fluorides, for example tetrabutylammonium fluoride, phosphonium fluorides, for example tetrabutylphosphonium fluoride, and mixtures thereof.

It is also possible to use complexes of the HF/tertiary amine type, such as pyridine/(HF)$_n$ or Et$_3$N/(HF)$_n$, n being from 1 to 10.

In a preferred embodiment, the catalyst is pyridine.

The following reaction (I)→(II) especially is carried out:

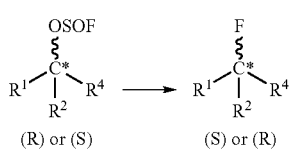

wherein, in the above formulae,
R$^1$, R$^2$ and R$^4$ each represents either a hydrogen atom or a group alkyl, alkenyl, alkynyl, which groups can be linear or branched, a group aryl, cycloalkyl, alkylcycloalkyl, —CO$_2$R$^5$, —(CH$_2$)$_n$—CO$_2$R$^5$, —COR$^5$, —SOR$^5$, —SO$_2$R$^5$, n being an integer preferably from 1 to 12,
R$^5$ being hydrogen or a group alkyl, alkenyl, alkynyl, which groups can be linear or branched, cycloalkyl, alkylcycloalkyl, aryl, especially substituted aryl;
it further being possible for R$^1$ to form an aromatic or non-aromatic heterocyclic group containing in place of one or more carbon atoms one or more hetero atoms selected from oxygen, sulfur and nitrogen;
R$^1$, R$^2$ and R$^4$ all being different.

There is carried out either the following reaction (Ia)→(IIa):

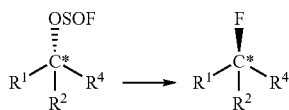

or the following reaction (Ib)→(IIb):

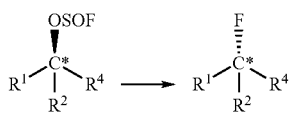

According to a preferred embodiment, the invention relates to a method for preparing a fluorinated molecule having a fluorine atom carried by an asymmetric carbon atom having a given configuration, located a to a ketone or ester group, in which method:
(i) there is introduced into a reactor a compound containing a fluorosulfite group having a given configuration at the C* carrying the fluorosulfite group, of formula (III)

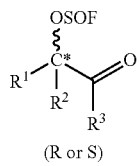

(R or S)

(2i) thermal decomposition of the fluorosulfite compound is carried out in the presence of a nucleophilic catalyst, preferably a catalyst containing a tertiary nitrogen atom,
(3i) the resulting fluorinated molecule, having the inverse configuration, of formula (IV) is recovered

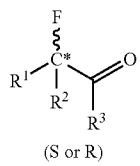

(S or R)

wherein:
$R^1$ represents a group alkyl, alkenyl, alkynyl, which groups can be linear or branched, a group aryl, cycloalkyl, alkylcycloalkyl, —$CO_2R^5$, —$(CH_2)_n$—$CO_2R^5$, —$COR^5$, —$SOR^5$, —$SO_2R^5$,
n being an integer preferably from 1 to 12,
$R^5$ being hydrogen or a group alkyl, alkenyl, alkynyl, which groups can be linear or branched, cycloalkyl, alkylcycloalkyl, aryl, especially substituted aryl;
it further being possible for $R^1$ to form an aromatic or non-aromatic heterocyclic group containing in place of one or more carbon atoms one or more hetero atoms selected from oxygen, sulfur and nitrogen;
$R^2$ represents hydrogen or a group corresponding to the definition given for $R^1$;
$R^1$ and $R^2$ are different;
$R^3$ represents hydrogen or a group $R^6$ or —$OR^6$, wherein $R^5$ is selected from the list given for $R^5$; it being possible for $R^6$ and $R^1$ to be identical or different.
In the invention, the alkyl, alkenyl and alkynyl groups can contain from 1 to 12 carbon atoms, preferably from 1 to 6 carbon atoms. The aryl, cycloalkyl, alkyl-cycloalkyl groups can contain from 3 to 8 carbon atoms, preferably from 5 to 6 carbon atoms. The heterocyclic compounds can contain from 3 to 8 atoms in the ring, preferably from 5 to 6.

$R^2$ can represent especially hydrogen.
$R^3$ can represent especially —$OR^6$.
$R^1$ can be especially a $C_1$-$C_{12}$-alkyl group, preferably a $C_1$-$C_6$-alkyl group, e.g. methyl.
$R^6$ can be especially a $C_1$-$C_{12}$-alkyl group, preferably a $C_1$-$C_6$-alkyl group, e.g. methyl.
According to a particular variant of the invention, the method is applied to the compounds of formula (III), of the lactate type, in which $R^1$ is methyl, $R^2$ is hydrogen and $R^3$ is —Oalkyl.
According to a particular form of the invention, $R^1$ is methyl, $R^2$ is hydrogen and $R^3$ is —OMe, and the configuration of the fluorinated molecule is the (R) configuration.
Particularly preferably, the mass of fluorosulfite compound (I), preferably of formula (III), that is used is substantially or totally free of HF and HCl.
Under the conditions of the invention, decomposition of the fluorosulfite compound is effected with inversion of configuration at the asymmetric carbon atom (stereoselective reaction).
The decomposition can be carried out either by gradually increasing the temperature of the mixture or by working at a fixed temperature.
Accordingly, the catalyst can be introduced into the fluorosulfite compound (I), preferably of formula (III), and then the temperature can be increased to a value sufficient to initiate decomposition, e.g. from 60 to 180° C., preferably from 100 to 150° C. The catalyst is therefore added to the fluorosulfite compound, which is at a temperature below the decomposition temperature leading to elimination of $SO_2$. The fluorosulfite compound can accordingly be employed, for example, at ambient temperature (approximately from 20 to 25° C.). A solvent can be used in that reaction, the fluorosulfite compound being introduced into the solvent, as well as the catalyst, and then the temperature is increased (definition of the solvent given hereinbelow).
In a method at fixed temperature, the fluorosulfite compound (I), preferably of formula (III), that is to be decomposed is added gradually to a reaction base brought to and maintained at a temperature suitable for the decomposition, e.g. from 60 to 180° C., preferably from 100 to 150° C., the catalyst being present in the base or added with or after the fluorosulfite. The base can contain a solvent or can be formed from a portion of the fluorosulfite compound, preferably of formula (III), or of the reaction mass that produced the fluorosulfite in a preceding step. This embodiment allows this step to be carried out continuously, by adjusting the admission of fluorosulfite compound to be decomposed and the removal of the reaction mass.
As solvent which can be used in those two embodiments there may be mentioned:
aliphatic hydrocarbons and more particularly paraffins, such as, especially, pentane, hexane, heptane, octane, isooctane, nonane, decane, undecane, tetra-decane, petroleum ether and cyclohexane; aromatic hydrocarbons such as, especially, benzene, toluene, xylenes, ethylbenzene, diethylbenzenes, trimethyl-benzenes, cumene, pseudocumene, petroleum fractions constituted by a mixture of alkylbenzenes, especially fractions of the Solvesso® type;
aliphatic or aromatic halogenated hydrocarbons, and mention may be made of: difluorobenzene, trifluoromethyl-benzene, fluorobenzene, monochlorobenzene, 1,2-dichlorobenzene, 1,3-dichlorobenzene, 1,4-dichlorobenzene, or mixtures thereof;
aliphatic, cycloaliphatic or aromatic ether oxides and, more especially, methyl tert-butyl ether, dipentyl oxide, diisopentyl oxide, ethylene glycol dimethyl ether (or 1,2-dimethoxyethane), diethylene glycol dimethyl ether (or 1,5-dimethoxy-3-oxa-pentane) or cyclic ethers, for example dioxane, tetrahydrofuran;

aliphatic or aromatic nitriles, such as acetonitrile, propionitrile, butanenitrile, isobutanenitrile, benzonitrile, benzyl cyanide;

N-methylpyrrolidone.

In a continuous method, the embodiment in which the fluorosulfite compound is fed into a medium maintained at the desired temperature is the preferred form.

The amount of catalyst employed is advantageously from 0.1 to 10 mol. %, based on the fluorosulfite compound, preferably from 0.1 to 2 mol. %. The procedure is preferably carried out under a pressure of from 50 mbar to 10 bar, more preferably from 1 to 10 bar.

When the decomposition is complete (which typically takes from several tens of minutes to several hours, e.g. from 1 to 5 hours), the medium can be cooled. It is then possible to carry out one or more washing steps with water, then to purify the washed crude product, for example by distillation in vacuo, before the pure product is recovered.

The fluorosulfite compound (III) can be obtained by reacting HF with the corresponding chlorosulfite compound (by definition, a compound containing a chlorosulfite group) of formula (V), containing a OSOCl group instead of the OSOF group in formula (III):

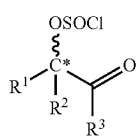

(V)

$R^1$, $R^2$ and $R^3$ having the same meanings as for formulae (III) and (IV).

The reaction is carried out in liquid HF medium.

According to this embodiment, from 1 to 10 equivalents of HF, based on the chlorosulfite compound, preferably from 1 to 5 equivalents, are generally used. It is preferred to add HF to the chlorosulfite compound. It is likewise preferred to work under an inert atmosphere, preferably under a nitrogen atmosphere. Absolute pressure is advantageously sufficient to maintain HF in the liquid state under the temperature conditions. That pressure can be, for example, from atmospheric pressure to 10 bar. The procedure is therefore advantageously carried out at a temperature of from −30 to 50° C., preferably from −10 to +20° C.

After introduction of the liquid HF, the medium is advantageously stirred at the desired temperature for a time sufficient to bring the reaction to completion, it being possible for that time typically to vary from 1 to 10 hours, depending on the reaction temperature.

In view of the subsequent decomposition step, it is preferable to remove residual HF and HCl that is formed. That can be achieved, for example, by working with nitrogen flushing (or flushing with a different inert gas) during the reaction. HF and HCl are preferably removed at the end of the reaction, for example by flushing with an inert gas (e.g. nitrogen), preferably combined with heating of the medium at a temperature that promotes removal of dissolved HF and HCl (a temperature of, for example, from 20 to 80° C., e.g. of the order of 50° C.) for several hours. HF and HCl can likewise be removed under reduced pressure.

The use of a solvent (e.g. as described above) during this step is not excluded, it being understood that it is preferred to work without a solvent.

The chlorosulfite compound can be obtained by reacting $SOCl_2$ with the corresponding hydroxylated precursor (VI) containing a OH group instead of the OSOCl group of the chlorosulfite compound:

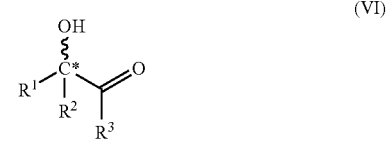

$R^1$, $R^2$ and $R^3$ having the same meanings as for formulae (III) and (IV).

The amount of $SOCl_2$ used is advantageously from 1 to 10 equivalents of $SOCl_2$, based on the hydroxylated precursor, preferably from 1 to 2 equivalents. The temperature is advantageously from −30 to +50° C., preferably from −10 to +20° C. In practice, it is preferred to pour the precursor gradually (typically within a period of from 1 to 10 hours) onto a base of $SOCl_2$. It is also preferred to work with nitrogen flushing. The base of thionyl chloride is preferably stirred during the addition of the precursor, and stirring is then advantageously maintained for the time to completion (typically from 1 to 10 hours).

The use of a solvent (e.g. as described above) in this step is not excluded, it being understood that it is preferred to work without a solvent.

Those methods for producing fluorosulfite on the one hand and chlorosulfite on the other hand can be used in order to obtain the totality of the fluorosulfite compounds of formula (I), starting from the chlorosulfite or from the hydroxylated precursor corresponding to the desired formula (I).

According to a particular embodiment, the following sequence of reactions is carried out, permitting the production of methyl (R)-2-fluoropropionate:

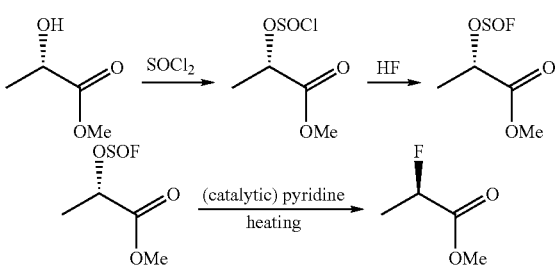

The sequence of reactions can be carried out in the same reactor or in different reactors.

Various routes for obtaining the fluorosulfite compounds and, in particular, the fluorosulfite compounds (III) can be envisaged. Among these, mention may be made of the route comprising the following steps:

(i) a compound of formula (VI) as defined above is reacted with a compound of formula (VII) $SOX_2$, wherein the substituents X represent identical or different halogen atoms, preferably selected from Cl, Br and F, to give a halosulfite compound of formula (VIII) having the same configuration

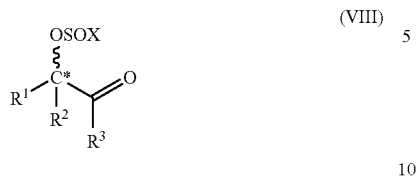

(2i) when one or both substituents X are other than F, the compound (Vil) is reacted with HF to give the fluorosulfite compound of formula (III).

When the substituents X in formula (VII) are Cl, the successive steps hydroxylated precursor→chlorosulfite compound→fluorosulfite compound described in detail above are recognised.

When the substituents X in formula (VII) are F, the fluorosulfite compound is obtained in a single step starting from the hydroxylated precursor (VI).

With SOFCl, the fluorosulfite compound is obtained substantially and directly.

In the embodiment for obtaining the fluorosulfite compound (III) using $SOX_2$ wherein X represents a halogen other than F or Cl, it is pointed out that the same operating conditions are used as in the route using $SOCl_2$ and then HF.

The invention will now be described in greater detail by means of the description of embodiments taken as non-limiting examples.

STEP 1

Formation of the Chlorosulfite Compound

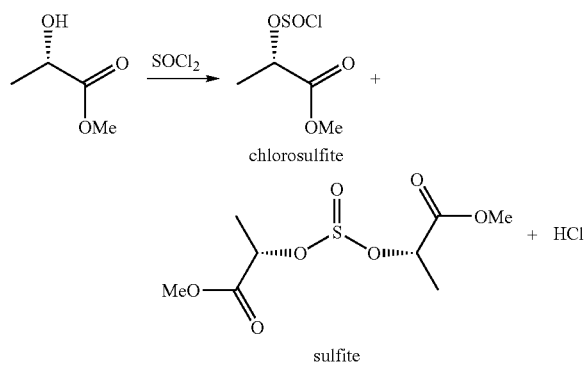

100 g of $SOCl_2$ (2 equivalents) are placed at the base of a reactor at 20° C. 43.8 g of methyl (S)-lactate are poured in within a period of 1 hour, with stirring and with nitrogen flushing. The degassed HCl is trapped in an aqueous sodium hydroxide solution.

6 hours after the end of pouring, the mixture has the following molar composition, determined by NMR (residual $SOCl_2$ has not been analysed):

residual methyl lactate: 0.1% (CR=99.9%)

chlorosulfite: 89.5% (yield=80.9%)

sulfite:10.5%

STEP 2

Obtaining the Fluorosulfite Compound

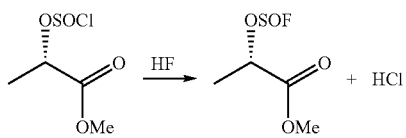

STEP 3

Decomposition of the Fluorosulfite Compound

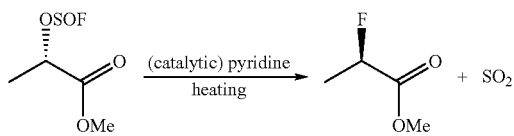

Steps 2 and 3 are carried out in succession starting from the solution of chlorosulfite compound prepared in step 1.

Fluorination is carried out at 10° C. in the course of 6 hours with 1.5 equivalents of HF, based on the chlorosulfite compound introduced. After stripping at 50° C. for 15 hours with nitrogen flushing, an amount of pyridine representing 1.5 mol. %, based on the intial chlorosulfite, is introduced. The temperature of the reactor is then brought to 140° C. and maintained at that level for 3 hours. During the decomposition, the pressure in the reactor is regulated at 2 bar. The mixture is then cooled, dichloromethane is added, and then washing is carried out twice with water. Quantitative analysis and chiral analysis are carried out by gas-phase chromatography.

Under those conditions, the yield of methyl fluoropropionate is 47%, based on the chlorosulfite compound used.

The optical purity in respect of the (R) enantiomer is 96.3%.

It must be understood that the invention defined by the accompanying claims is not limited to the particular embodiments indicated in the description above but includes variants thereof that do not depart from either the scope or the spirit of the present invention.

The invention claimed is:

1. A stereoselective method for preparing a fluorinated molecule having a fluorine atom carried by an asymmetric carbon atom having the (R) or (S) configuration, located a to an ester or ketone group, said method comprising:

(i) introducing into a reactor a single enantiomer of a fluorosulfite compound having a given configuration at the C* carrying the fluorosulfite group, of formula (III)

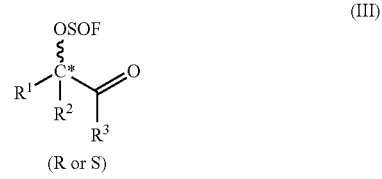

(2i) conducting thermal decomposition of the fluorosulfite compound in the presence of a nucleophilic catalyst, and (3i) recovering the resulting single enantiomer fluorinated molecule, having the inverse configuration at the C*, of formula (IV)

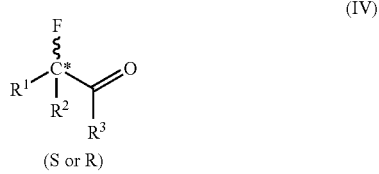

(S or R)

wherein:

C* represents a chiral carbon;

$R^1$ represents an alkyl, alkenyl or alkynyl group, which is linear or branched, or an aryl, cycloalkyl or alkylcycloalkyl group, $-CO_2R^5$, $-(CH_2)_n-CO_2R^5$, $-COR^5$, $-SOR^5$ or $-SO_2R^5$;

n is an integer from 1 to 12;

$R^5$ is hydrogen or an alkyl, alkenyl or alkynyl group, which is linear or branched, or a cycloalkyl, alkylcycloalkyl, aryl or substituted aryl group;

or $R^1$ forms an aromatic or non-aromatic heterocyclic ring having in place of one or more carbon atoms one or more hetero atoms selected from the group consisting of oxygen, sulfur and nitrogen;

$R^2$ represents hydrogen or a member selected from the group defined for $R^1$;

$R^1$ and $R^2$ are different; and $R^3$ represents hydrogen or a group $R^6$ or $-OR^6$, wherein $R^6$ is a member selected from the group defined for $R^5$, wherein $R^6$ and $R^1$ are identical or different.

2. The method according to claim 1, $R^3$ represents $-OR^6$.

3. The method according to claim 1, in which $R^6$ is a $C_1$-$C_{12}$-alkyl group.

4. The method according to claim 3, in which $R^6$ is a $C_1$-$C_6$-alkyl group.

5. The method according to claim 3, in which $R^6$ is methyl.

6. The method according to claim 1, in which $R^1$ is methyl, $R^2$ is hydrogen and $R^3$ is —O-alkyl.

7. The method according to claim 1, in which $R^3$ is —OMe.

8. The method according to claim 1, in which $R^2$ represents hydrogen.

9. The method according to claim 1, in which $R^1$ is a $C_1$-$C_{12}$-alkyl group.

10. The method according to claim 9, in which $R^1$ is methyl.

11. The method according to claim 1, in which the catalyst is a compound having a tertiary nitrogen atom, a fluoride anion source, or a mixture or complex thereof.

12. The method according to claim 11, in which the catalyst is selected from the group consisting of triethylamine, diisopropylethylamine, tri-n-propylamine, tri-n-butylamine, methyldibutylamine, methyldicyclohexylamine, ethyldiisopropylamine, N,N-diethylcyclohexylamine, pyridine, 4-dimethylaminopyridine, N-methylpiperidine, N-ethylpiperidine, N-n-butylpiperidine, 1,2-dimethylpiperidine, N-methylpyrrolidine, 1,2-dimethylpyrrolidine, dimethylaniline, and picoline, and mixtures thereof.

13. The method according to claim 11, in which the catalyst is selected from the group consisting of amides and formamides having a tertiary nitrogen atom, urea derivatives, basic fluorides, ammonium fluorides and phosphonium fluorides.

14. The method according to claim 11, in which the catalyst is pyridine.

15. The method according to claim 1, in which the mass of fluorosulfite compound employed is substantially or totally free of HF and HCl.

16. The method according to claim 1, in which the catalyst is introduced into the fluorosulfite compound and then the temperature is increased to 60 to 180° C.

17. The method according to claim 16, in which the temperature is increased to 100 to 150° C.

18. A stereoselective method according to claim 1, wherein the fluorosulfite compound is added gradually to a solvent heated to a temperature of from 60 to 180° C., with the catalyst being present in the solvent or being added with or after the fluorosulfite compound.

19. The method according to claim 18, in which the temperature is from 100 to 150° C.

20. The method according to claim 1, in which the amount of catalyst employed is from 0.1 to 10 mol. %, based on the fluorosulfite compound.

21. The method according to claim 20, in which the amount of catalyst employed is from 0.1 to 2 mol. %, based on the fluorosulfite compound.

22. The method according to claim 1, in which the procedure is carried out under a pressure of from 50 mbar to 10 bar.

23. The method according to claim 22, in which the procedure is carried out under a pressure of from 1 to 10 bar.

24. A stereoselective method according to claim 1, wherein the fluorosulfite compound is obtained by reacting HF with the corresponding chlorosulfite compound having an OSOCl group instead of the OSOF group.

25. The method according to claim 24, in which there are employed from 1 to 10 equivalents of HF, based on the chlorosulfite compound.

26. The method according to claim 25, in which there are employed from 1 to 5 equivalents of HF, based on the chlorosulfite compound.

27. The method according to claim 24, in which HF is added to the chlorosulfite compound.

28. The method according to claim 24, in which the procedure is carried out under an inert atmosphere.

29. The method according to claim 24, in which the procedure is carried out at a temperature of from −30 to +50° C.

30. The method according to claim 29, in which the procedure is carried out at a temperature of from −10 to +20° C.

31. The method according to claim 24, in which HF and HCl are removed at the end of the reaction between HF and the chlorosulfite compound.

32. The method according to claim 24, in which the chlorosulfite compound is obtained by reacting $SOCl_2$ with the corresponding hydroxylated precursor having a OH group instead of the OSOCl group.

33. The method according to claim 32, in which the procedure is carried out with an amount of $SOCl_2$ of from 1 to 10 equivalents of $SOCl_2$, based on the hydroxylated precursor.

34. The method according to claim 33, in which the procedure is carried out with an amount of $SOCl_2$ of from 1 to 2 equivalents of $SOCl_2$, based on the hydroxylated precursor.

35. The method according to claim 32, in which the procedure is carried out at a temperature of from −30 to +50° C.

36. The method according to claim 35, in which the procedure is carried out at a temperature of from −10 to +20° C.

37. The method according to claim 32, in which the precursor is poured gradually onto a base of $SOCl_2$.

38. The method according to claim 32, in which the procedure is carried out with nitrogen flushing.

39. The method according to claim 32, comprising:

a) reacting (S)-methyl 2-hydroxypropionate

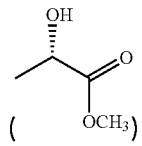

with thionyl chloride to yield (S)-1-(methoxycarbonyl)ethyl chlorosulfinate

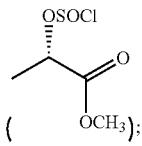

b) reacting (S)-1-(methoxycarbonyl)ethyl chlorosulfinate with hydrogen fluoride to yield (S)-1-(methoxycarbonyl)ethyl fluorosulfinate

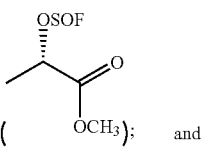 and c) reacting (S)-1-(methoxycarbonyl)ethyl fluorosulfinate with a catalytic amount of pyridine with heating to yield (R)-methyl 2-fluoropropionate

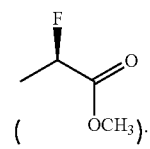

40. The method according to claim 39, in which the sequence of reactions is carried out in the same reactor or in different reactors.

* * * * *